(12) United States Patent
Donnan et al.

(10) Patent No.: US 6,454,745 B1
(45) Date of Patent: Sep. 24, 2002

(54) SEAL

(75) Inventors: Jeremy Francis Donnan, Balerno; John Targell, Kilmarnock, both of (GB)

(73) Assignee: NMT Group, PLC, Livingston (GB)

( * ) Notice: Subject to any disclaimer, the term of this patent is extended or adjusted under 35 U.S.C. 154(b) by 130 days.

(21) Appl. No.: 09/707,176

(22) Filed: Nov. 6, 2000

(30) Foreign Application Priority Data

Nov. 10, 1999 (GB) .............................................. 9926505

(51) Int. Cl.⁷ ................................................ A61M 5/00
(52) U.S. Cl. ......................... 604/181; 604/207; 604/232
(58) Field of Search ................................. 604/181, 154, 604/198, 218, 414, 207, 232, 249, 110, 93, 41.1, 240, 190, 206

(56) References Cited

U.S. PATENT DOCUMENTS

| | | | | |
|---|---|---|---|---|
| 3,974,832 A | * | 8/1976 | Kruck ......................... 604/206 |
| 4,365,626 A | * | 12/1982 | House ......................... 604/190 |
| 4,548,329 A | | 10/1985 | Curry .......................... 215/216 |
| 4,781,701 A | * | 11/1988 | Geprags ....................... 604/240 |
| 5,224,939 A | | 7/1993 | Holman et al. .............. 604/283 |
| 5,295,658 A | | 3/1994 | Atkinson et al. ........ 251/149.1 |
| 5,575,769 A | | 11/1996 | Vaillancourt .................. 604/86 |
| 5,637,092 A | * | 6/1997 | Shaw .......................... 604/110 |
| 5,690,612 A | * | 11/1997 | Lopez et al. .................... 604/93 |
| 5,772,652 A | * | 6/1998 | Zielinski ..................... 604/411 |
| 5,785,693 A | * | 7/1998 | Haining ...................... 604/249 |
| 6,017,331 A | * | 1/2000 | Watts et al. ................. 604/232 |
| 6,096,010 A | * | 8/2000 | Walters et al. .............. 604/207 |
| 6,174,304 B1 | * | 1/2001 | Weston ........................ 604/414 |
| 6,213,985 B1 | * | 4/2001 | Niedospial, Jr. ............ 604/218 |
| 6,287,282 B1 | * | 9/2001 | Bonaldo et al. ............. 604/198 |
| 6,322,535 B1 | * | 11/2001 | Hitchins et al. ............. 604/154 |

FOREIGN PATENT DOCUMENTS

| | | | |
|---|---|---|---|
| EP | 0 259 582 | 3/1988 | |
| EP | 0 738 520 | 10/1996 | .......... A61M/39/10 |
| GB | 2 217 695 | 11/1989 | .......... B65D/51/18 |
| WO | WO 95/17873 | 7/1995 | |
| WO | WO 98/52631 | 11/1998 | ............ A61M/5/00 |

* cited by examiner

Primary Examiner—Teresa Walberg
Assistant Examiner—Leonid M. Fastovsky
(74) Attorney, Agent, or Firm—Bracewell & Patterson, LLP

(57) ABSTRACT

A seal adapted to be fitted over the open end of the barrel of a hypodermic syringe has a cap of a non-latex elastomer having a central aperture which is sufficiently small as ordinarily to retain liquid therebehind but which can be deformably expanded to allow passage of the rearward end of a needle hub for engagement with the barrel.

23 Claims, 2 Drawing Sheets

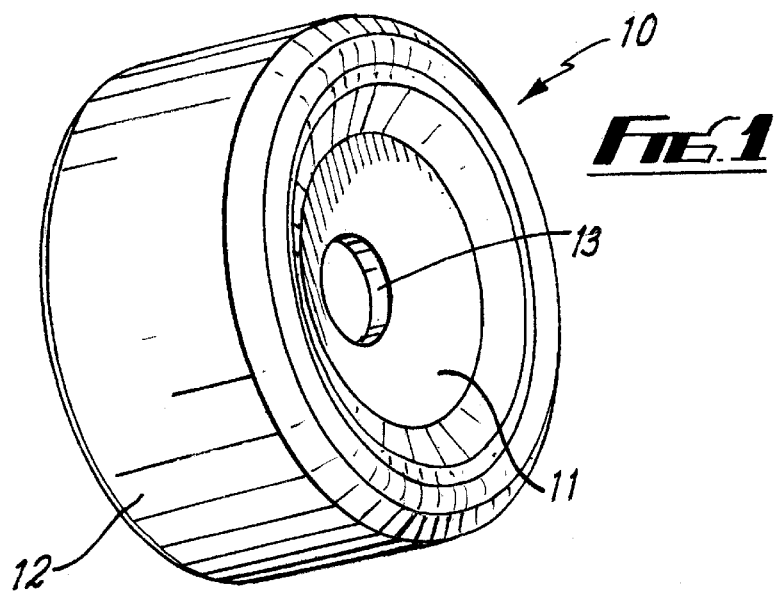
FIG. 1
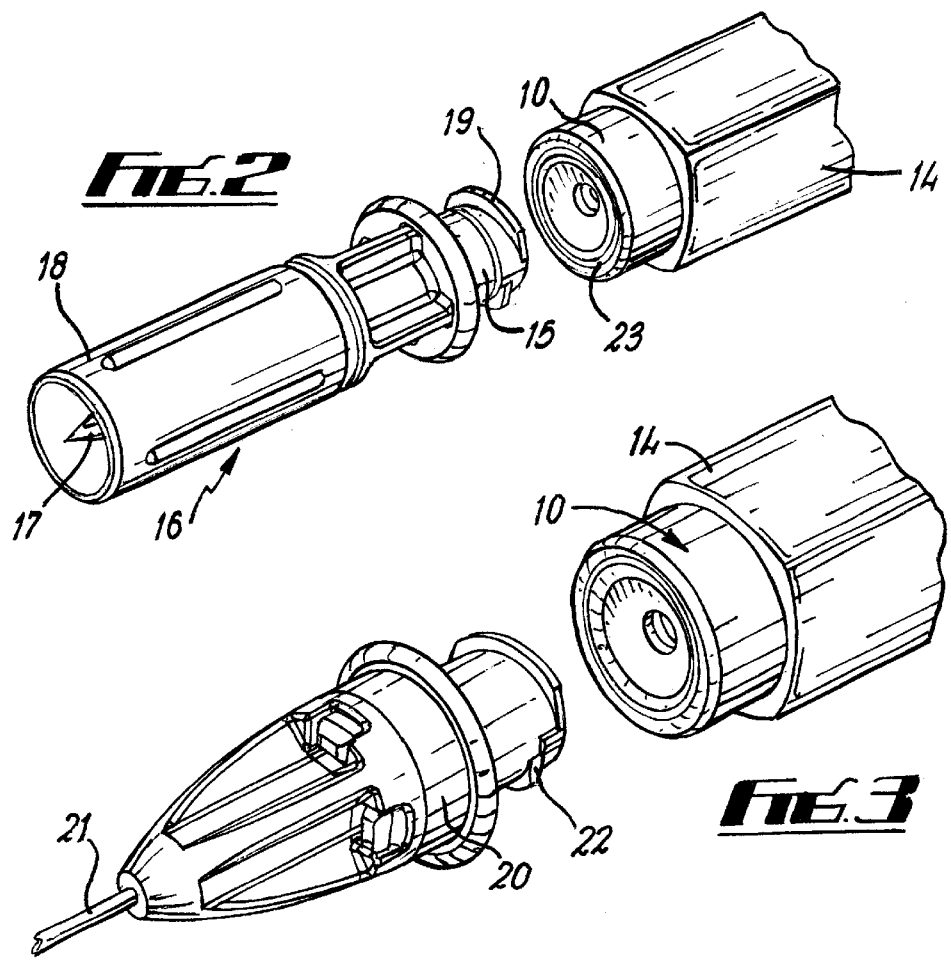
FIG. 2
FIG. 3

SEAL

This invention relates to the fitting of needle components to the barrel of a hypodermic syringe.

It is common practice to fit a syringe with a filling needle for the purpose of drawing liquid into the barrel of the syringe by retraction of its plunger from a vial often of the kind having a rubber cap which is penetrated by the filling needle. After the syringe has been charged, the filling needle is removed and replaced by a needle to be used for administration of an injection into a patient. Yet again it is often necessary to change a needle to meet patient requirements.

During the change of needle where the syringe is of a type having a large open end to permit needle retraction, care must be taken to avoid spillage of the contents of the syringe through the open end of the barrel.

It is an object of the present invention to provide a seal for the open end of a syringe barrel which overcomes the problem aforesaid.

According to the present invention there is provided a seal adapted to be fitted over the open end of the barrel of a hypodermic syringe comprising a cap of a non-latex elastomer having a central aperture which is sufficiently small as ordinarily to retain liquid therebehind but which can be deformably expanded to allow passage of a needle mounting portion for engagement with the barrel.

The cap may be of silicone rubber.

The aperture may be circular.

The aperture may take the form of a number of slits extending radially outward from the centre of the cap.

The cap may comprise a circular disc having a cylindrical skirt extending from its rear face.

The internal periphery of the skirt may be provided with axially spaced circumferential ribs adapted to engage with circumferential grooves on the end of the barrel to hold the cap in position.

The invention also includes a syringe barrel fitted with a seal as aforesaid.

The syringe barrel may be used with both a filling needle assembly and an injection needle assembly in which case the cap is expandable to allow fitting of both the filling needle and the injection needle to the barrel.

The arrangement may be such that the mounting portion of the injection needle is engaged with the barrel through a one-way coupling means formed by interfitting components on the needle mounting portion and the barrel whereby the injection needle once assembled to the barrel cannot be disengaged from the barrrel (at least not without damaging the components). The filling needle may also be engageable with the barrel with the aid of the one-way coupling means associated with the barrel but in such a way that the filling needle may be subsequently disengaged.

The one way coupling means may comprise a threaded connection or a bayonent-type connection between a male part and a female part, one part being associated with the barrel and the other part being associated with the barrel.

The one way coupling means may for example comprise a threaded connection between a male and a female part, there being a void in an upstanding portion of the thread on each part and a barb in the void on one of the parts, the arrangement being such that when the parts are threadedly engaged, resilient deformation of at least one of the parts enables the barb to latch behind an end of a thread at the void in the other of the parts to prevent subsequent disconnection of the parts.

Another aspect of the invention concerns a threaded connection between a male part and a female part which, when properly threadedly engaged, cannot be disconnected, particularly, though by no means exclusively, suitable for joining components of fluid handling medical devices such as syringes, cannulas and catheters for example.

According to this aspect of the invention there is provided a threaded connection between a male and a female part, there being a void in an upstanding portion of the thread on each part and a barb in the void on one of the parts, the arrangement being such that when the parts are threadedly engaged, resilient deformation of at least one of the parts enables the barb to latch behind an end of a thread at the void in the other of the parts to prevent subsequent disconnection of the parts.

There may be on each part a two-start thread, the upstanding portion of each thread having a circumferential extent of less than 180° whereby there are voids between the ends of the two threads on each part and diametrically opposed barbs in the voids on the male part.

The height of each thread on the female part may increase from one end to the other which provides the abutment against which a barb latches.

The invention will be further apparent from the following description by way of example with reference to the figures of the accompanying drawing, in which:

FIG. 1 is a perspective view of the resiliently-deformable sealing cap associated with the barrel of a hypodermic syringe;

FIG. 2 is a fragmentary perspective view of a syringe barrel fitted with the cap and about to receive a filling needle device;

FIG. 3 is a view similar to that of FIG. 2 but wherein the barrel is about to receive the hub of an injection needle;

Figure 4:
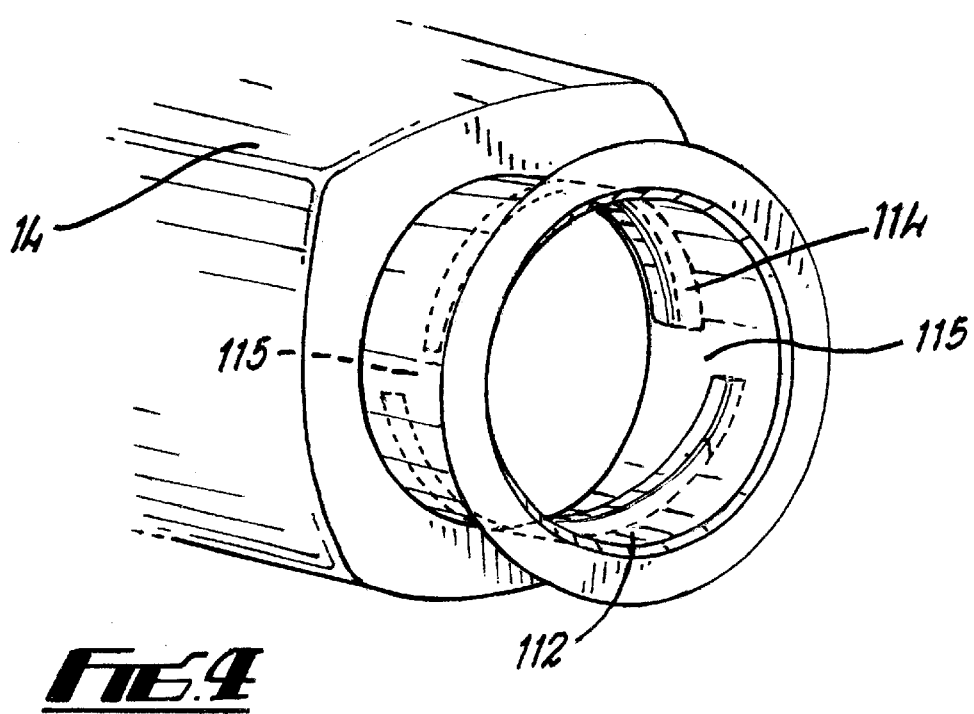
FIG. 4 is a perspective view of the forward end of a syringe barrel on an enlarged scale and with the resilient cap omitted.

Referring firstly to FIG. 1, it will be seen that the seal, generally indicated at 10, comprises a cap having a circular disc portion 11 and a cylindrical skirt 12 extending from the rear face of the disc portion 11. A circular aperture 13 is provided through the centre of the disc portion 11. The seal 10 is a moulding of silicone rubber.

The inner periphery of the skirt 12 is provided with axially spaced circumferential ribs (not shown) which engage circumferential grooves. on the forward end part of a syringe barrel 14 to enable the cap to fit securely over the open end of the barrel.

The aperture 13 is sufficiently small as to retain liquid therebehind having regard to the surface tension of the liquid even if the barrel 14 is pointed downwardly without deliberate violent movement such as shaking.

The aperture 13 may be resiliently expanded to permit entry of the mounting portion 15 of a filling needle assembly 16 whose needle 17 is protected until required by use by a frangible guard 18 (see FIG. 2). The rearward end 15 has a screw thread 19 which engages a complimentary thread (not shown) within the barrel 14 such that a raised sealing lip 23 of the seal is compressed between the mounting portion 15 and barrel 14 to form a tight seal.

After the barrel has been filled by insertion of the needle 17 into a vial of liquid which is drawn into the barrel 14 by retraction of the syringe plunger (not shown) the filling needle device 16 is disengaged and discarded and an injection needle 21 is fitted to the barrel. The hub or mounting portion 20 of the injection needle 21 also has a screw thread 22 which engages the thread within the barrel 14 again compressing the cap between the parts to form a seal.

During the needle change, i.e. during the interval between detachment of the filling needle device and fitting of the injection needle, the aperture 13 relaxes to its original size preventing accidental spillage of liquid from the barrel 14.

Figure 5:
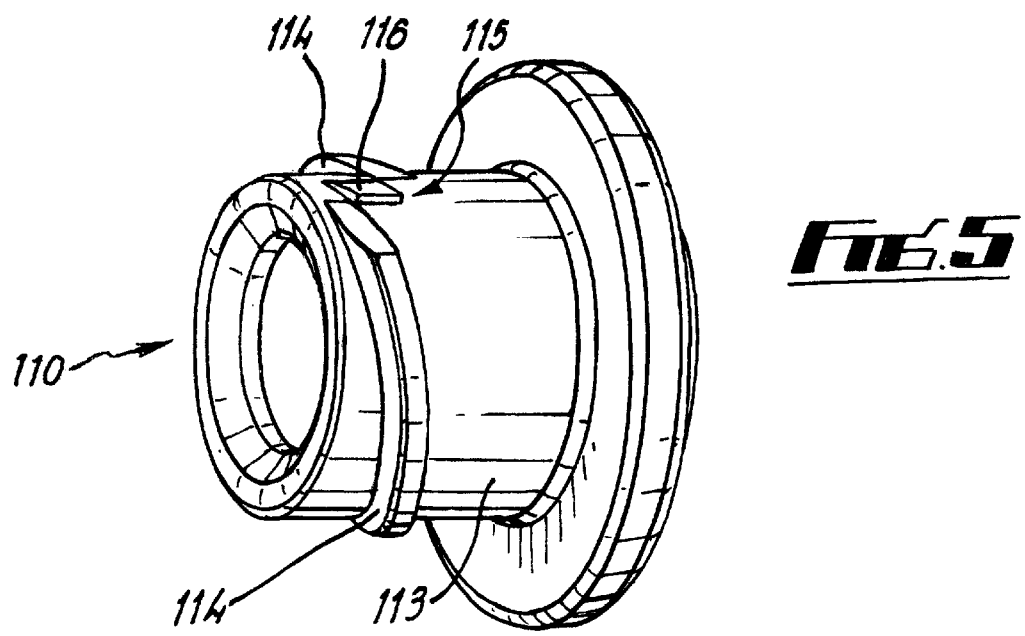
FIG. 5 is a perspective view on an enlarged scale of a connector arrangement for permanently coupling the injection needle to the syringe barrel.

Referring now to FIGS. 4 and 5, a one way coupling means in the form of a threaded connection is illustrated. The coupling comprises a threaded female socket part 112 at the forward end of the barrel 14 adapted to receive a threaded male part 113 of a mounting portion 110 of the needle assembly. Each of the parts 112 and 113 is provided with a two-start right handed thread. The upstanding portion 114 of each of the four threads has a circumferential extent of less than 180° whereby there are voids 115 between the ends of the two threads on each part. On the part 113 are diametrically opposed barbs 116 in the voids 115.

When the parts are threadedly connected the barbs 116 are introduced to the voids 115 on the part 112 before relatively rotating the two parts. During rotation the part 112 which is of a plastics material resiliently deforms as the barbs 116 override the portions 114 of the threads on the part 112 before the barbs latch behind the ends of the threads on the part 112 to lock the parts 112 and 113 against disconnection. In this manner, the injection needle assembly is permanently coupled to the barrel and cannot be uncoupled without damaging the coupling connector 110.

It will be understood that the seal 10 will be present during fitting of the needle assembly to the barrel, i.e. in the course of engaging the male part 113 to the female part 112, the male part 113 will be passed through the aperture 13 in the seal 10 with consequent expansion of the aperture 13 to accommodate the male part.

The height of each thread on the female part increases from one end to the other which provides the abutment against which the barbs 116 latch to facilitate the threading operation and deformation of the part 112.

Whilst the injection needle assembly may be fitted to the barrel in a permanent fashion as described above, the filling needle assembly is releasably connected to the barrel so that it can be used in filling the barrel and then removed and replaced by the injection needle assembly. Fitting of the filling needle assembly may be through a coupling means 110 similar to that illustrated in FIGS. 4 and 5 except for the omission of the locking barbs 116. In other words, the part 112 of the barrel will be utilised and the mounting portion of the filling needle assembly will have the configuration of part 113 except for the omission of the barbs 116 thereby allowing the filling needle assembly to fitted to the barrel through the sealing cap 10 and subsequently disengaged following filling of the syringe barrel.

Although in FIGS. 4 and 5, the female part 112 is shown as being associated with the barrel and the male part 113 with the needle assembly, the arrangement may be reversed so that the male part is associated with the barrel and the female part with the injection or filling needle assembly.

It will be appreciated that it is not intended to limit the invention to the above examples only, many variations, such as might readily occur to one skilled in the art, being possible, without departing from the scope thereof.

What is claimed is:

1. A hypodermic syringe barrel provided with a seal adapted to be fitted over the open end of the barrel thereof, the seal comprising a cap of a non-latex elastomer having a central aperture which is sufficiently small as ordinarily to retain liquid therebehind but which can be deformably expanded to allow passage of a mounting portion of a needle for engagement with the barrel.

2. A seal adapted to be fitted over the open end of the barrel of a hypodermic syringe comprising a cap of a non-latex elastomer having a central aperture which is sufficiently small as ordinarily to retain liquid therebehind but which can be deformably expanded to allow passage of a mounting portion of a needle for engagement with the barrel.

3. A syringe barrel as claimed in claim 1 in which the cap is of silicone rubber.

4. A syringe barrel as claimed in claim 1 in which the aperture is circular.

5. A syringe barrel as claimed in claim 1 in which the aperture takes the form of a number of slits extending radially outward from the centre of the cap.

6. A syringe barrel as claimed in claim 1 in which the cap comprises a circular disc having a cylindrical skirt extending from its rear face.

7. A syringe barrel as claimed in claim 6 in which the internal periphery of the skirt is provided with axially spaced circumferential ribs adapted to engage with circumferential grooves on the end of the barrel to hold the cap in position.

8. A syringe barrel as claimed in claim 1 in which the needle forms part of a needle filling assembly.

9. A syringe barrel as claimed in claim 1 in which the needle forms part of a an injection needle assembly.

10. A barrel as claimed in claim 1, containing liquid which is retained from spillage by the seal if the barrel is pointed downwardly.

11. In combination, a syringe barrel as claimed in claim 1, a needle filling assembly and an injection needle assembly, said assemblies each having a mounting portion for insertion through the seal of the aperture for engagement with the barrel.

12. The combination of claim 11 in which the mounting portion of each assembly is engageable with the same coupling formation on the barrel, the coupling formation being accessible through the seal aperture.

13. The combination of claim 12 in which the mounting portion of the filling needle assembly is releasably engageable with said formation while the mounting portion of the injection needle assembly is non-releasably engageable with said formation .

14. The combination of claim 13 in which the mounting portions and said formation engage via a threaded connection.

15. The combination of claim 13 in which the mounting portions and said formation engage via a bayonet connection.

16. The combination of claim 14 in which the injection needle mounting portion and the barrel are provided one with a male part and the other with a female part and are coupled together through a threaded connection between said male and a female parts, there being a void in an upstanding portion of the thread on each part and a barb in the void on one of the parts, the arrangement being such that when the parts are threadedly engaged, resilient deformation of at least one of the parts enables the barb to latch behind an end of a thread at the void in the other of the parts to prevent subsequent disconnection of the parts.

17. The combination of claim 16 in which, on each part, there is a two-start thread, the upstanding portion of each thread having a circumferential extent of less than 180° whereby there are voids between the ends of the two threads on each part and diametrically opposed barbs in the voids on the male part.

18. A method of preventing spillage of liquid from the open end of the barrel of a hypodermic syringe comprising fitting the open end of the barrel with a seal comprising a cap of a non-latex elastomer having a central aperture which is sufficiently small as ordinarily to retain liquid therebehind and fitting a needle assembly to the barrel by insertion of a mounting portion thereof through the aperture so as to deformably expand the seal to allow passage of said mounting portion for engagement with the barrel.

19. A method of preparing a hypodermic syringe for use in the administration of an injection comprising fitting the open end of the barrel of the syringe with a seal comprising a cap of a non-latex elastomer having a central aperture which is sufficiently small as ordinarily to retain liquid therebehind, coupling a filling needle assembly to the barrel so that a mounting portion of the assembly passes through the central aperture in the seal, operating the syringe to draw liquid into the barrel through the filling needle assembly, removing the latter with accompanying withdrawal of its mounting portion through the central aperture with consequent expansion of the central aperture during such removal and subsequent relaxation of the central aperture to a size consistent with preventing spillage from the barrel if the latter is pointed downwardly, and fitting an injection needle assembly having a hub by inserting the hub thereof through the central aperture of the seal with consequent expansion of the central aperture during such insertion.

20. A method as claimed in claim 19 in which both needle assemblies are engageable with the same formation on the barrel, the filling needle assembly being releasably engageable with said formation and the injection needle assembly being non-releasably engageable with the barrel.

21. A threaded connection between a male and a female part, there being a void in an upstanding portion of the thread on each part and a barb in the void on one of the parts, the arrangement being such that when the parts are threadedly engaged, resilient deformation of at least one of the parts enables the barb to latch behind an end of a thread at the void in the other of the parts to prevent subsequent disconnection of the parts.

22. A connection as claimed in claim 21 in which, on each part, there is a two-start thread, the upstanding portion of each thread having a circumferential extent of less than 180° whereby there are voids between the ends of the two threads on each part and diametrically opposed barbs in the voids on the male part.

23. A connection as claimed in claim 22 in which the height of each thread on the female part may increase from one end to the other which provides the abutment against which a barb latches.

* * * * *